United States Patent [19]

Nagel

[11] Patent Number: 4,585,759

[45] Date of Patent: Apr. 29, 1986

[54] ANTIBACTERIAL DERIVATIVES OF A NEUTRAL MACROLIDE

[75] Inventor: Arthur A. Nagel, Gales Ferry, Conn.

[73] Assignee: Pfizer inc., New York, N.Y.

[21] Appl. No.: 693,702

[22] Filed: Jan. 22, 1985

[51] Int. Cl.$^4$ .................. A61K 31/71; C07H 17/08
[52] U.S. Cl. ................................ 514/29; 536/7.2
[58] Field of Search .............. 536/7.2, 7.3, 7.9; 424/180; 514/29

[56] References Cited

U.S. PATENT DOCUMENTS 3,857,937 12/1974 Mancy et al. .................. 424/120

FOREIGN PATENT DOCUMENTS 0151598 11/1980 Japan .................. 536/7.4

OTHER PUBLICATIONS

Arnoux, et al., J. Am. Chem. Soc., 102, 3605 (1980).

Primary Examiner—Johnnie R. Brown
Assistant Examiner—Elli Peselev
Attorney, Agent, or Firm—Charles J. Knuth; Albert E. Frost; James M. McManus

[57] ABSTRACT

New antibacterial agents from a neutral macrolide wherein the keto group of the beta-D-4,6-dideoxy-3-ketoallose unit is converted to the corresponding hydroxy, amino, methylamino and dimethylamino functions.

4 Claims, No Drawings

ANTIBACTERIAL DERIVATIVES OF A NEUTRAL MACROLIDE

BACKGROUND OF THE INVENTION

This invention relates to new antibacterial agents which are derivatives of a neutral macrolide previously disclosed in U.S. Pat. No. 3,857,937 and J. Am. Chem. Soc., 102, 3605 (1980). The novel compounds of the present invention represent changes in the ketone function of the beta-D-4,6-dideoxy-3-ketoallose unit of the macrolide structure.

SUMMARY OF THE INVENTION

This invention provides new macrolide antibacterial compounds selected from those of the formula

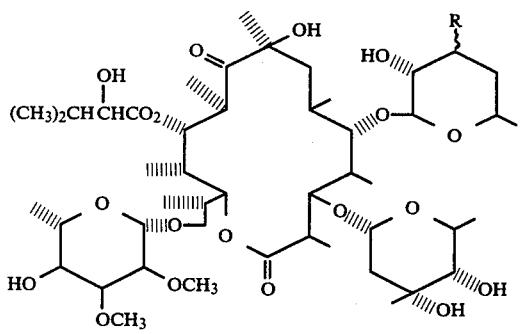

wherein R is selected from the group consisting of hydroxy, amino, methylamino and dimethylamino. Pharmaceutically-acceptable acid addition salts of the aforementioned compounds wherein R is amino, methylamino or dimethylamino are also considered part of the present invention.

Preferred are those compounds where R is dimethylamino; especially preferred is the compound where R is dimethylamino in the beta configuration.

Also considered as part of the present invention is a method for treating a bacterial infection in a mammalian subject, which comprises administering to said subject an antibacterially effective amount of a compound of the present invention; and a pharmaceutical composition which comprises a pharmaceutically-acceptable carrier and a compound of the present invention wherein said pharmaceutically-acceptable carrier and said compound are present in a weight ratio in the range of from 1:6 to 6:1.

DETAILED DESCRIPTION OF THE INVENTION

The neutral macrolide from which the compounds of the present invention are derived has the following chemical structure:

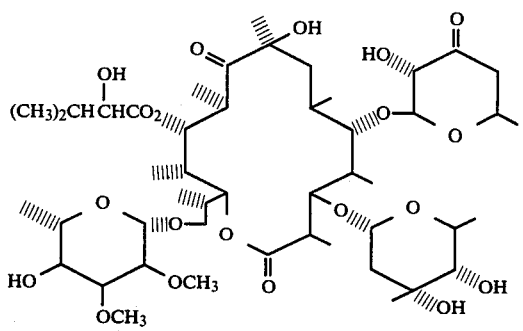

The chemical name for this compond is 6.12-dideoxy-15-[(6-deoxy-2,3-di-O-methyl-beta-D-allopyranosyl)-oxy 9-5-0-(4,6-dideoxy-beta-D-erythro-hexopyranos-3-ulos-1-yl)-3-0-(2,6-dideoxy-3-C-methyl-alpha-L-ribohexopyranosyl)-8-hydroxy-14-methyl-erythronolide (14S)-11-(2-hydroxy-3-methylbutanoate). In the interest of brevity this neutral macrolide will be referred to as CP-63,693. Further, in describing the chemistry leading to the compounds of the present invention only that portion of the structure where changes take place, namely the beta-D-4,6-dideoxy-3-ketoallose portion, will be depicted.

Treatment of the neutral macrolide CP-63,693 with a ten to fifteen fold excess of ammonium chloride or methylamine hydrochloride in the presence of hydrogen gas and a palladium-on-charcoal catalyst results in the formation of the corresponding $C_3'$ amino and methylamino derivatives, respectively. The reaction is depicted as follows:

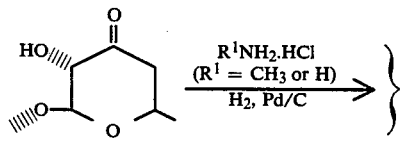

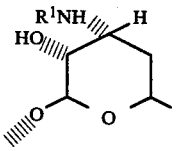

1

This reductive amination reaction is best conducted in a reaction-inert solvent such as methanol or ethanol. The reaction can be conducted at room temperature at a hydrogen pressure of about 146 kg. s. cm. Under these conditions the reaction is generally complete in about 6–18 hours.

As is realized, such a reduction can theoretically give rise to the formation of two diastereomers; a substituent on the same side of the ring as the adjacent $C_2'$ hydroxy group would have the alpha configuration, which is represented by a broken line, and a substituent on the opposite side of the hydroxy group having the beta configuration, which is represented by a solid line. When both diastereomers are depicted they can be represented by a wavy line.

In the particular reductive amination wherein hydrogen gas is used and palladium-on-charcoal is employed as the catalyst only one of the diastereomers is found. Based on analytical and other findings the isolated diastereomer in each case is assigned the alpha configuration.

When the neutral macrolide CP-63,693 is reacted with ammonium chloride or methylamine and sodium cyanoborohydride is employed as the reducing agent both diastereomers, 1 and 2, are formed, as follows:

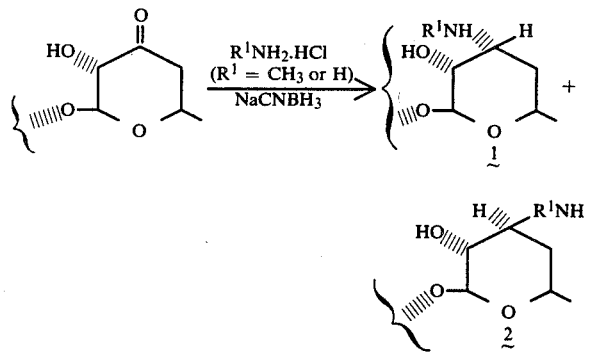

The reaction is best conducted in a reaction-inert solvent such as methanol using a 50 percent molar excess of ammonium chloride or methylamine hydrochloride. The use of an equimolar amount of hydride to marcolide will provide the desired product, but an excess as large as 75% provides an optimum yield of product. Using the aforementioned ratio of starting reagents and conducting the reaction at room temperature provides product after a reaction period of 2-3 hours.

Treatment of 1 ($R=CH_3NH-$) with equimolar amounts of formaldehyde and formic acid in a reaction-inert solvent such as chloroform at room temperature results in the formation of an oxazolidine ring between the methylamine moiety and the adjacent hydroxy group as follows:

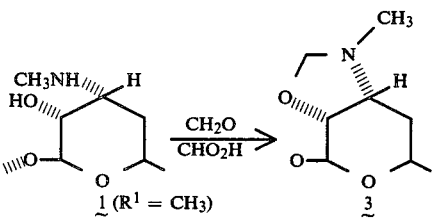

Hydrogenation of 3 with hydrogen gas and a palladium-on-charcoal catalyst at room temperature at 50 p.s.i. provides the alpha-dimethylamino diastereomer of the present invention as follows:

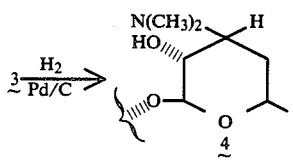

Treatment of the mixture of 1 and 2 with formaldehyde in chloroform as the reaction-inert solvent results in the conversion of 1 ($R'=CH_3$) to 3 and allows for the separation of the less basic oxazolidine 3 from 2 by selective extraction at pH 2.5.

Reaction of the separated beta-diastereomer 2 ($R^1=CH_3$) with formaldehyde and formic acid in chloroform provides, directly, the beta-dimethylamino diastereomer of the present invention, depicted as follows:

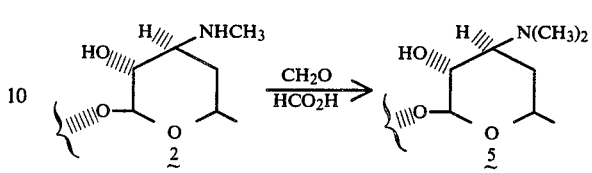

Reaction of CP-63,693 with a two fold molar excess of sodium borohydride at room temperature in a reaction-inert solvent gives a mixture of both the $C_3'$-equatorial and axial alcohol, 6, as follows:

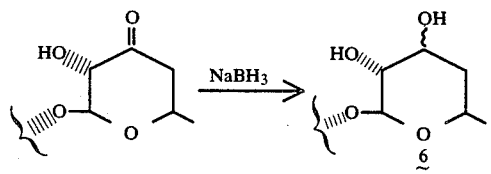

The use of a hindered hydride, such as lithium tri-t-butoxyaluminum hydride, with CP-63,693 gives a single diastereomer, 7, the alpha —$C_3'$ hydroxy as follows:

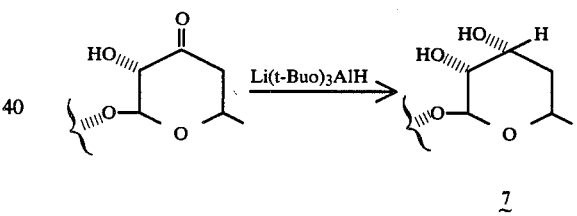

The most useful reaction-inert solvent in the hydride reactions to give the hydroxy compounds of the present invention is tetrahydrofuran. The molar ratio of hydride to macrolide is generally about 2:1. The reaction, when conducted at room temperature is generally complete in a few hours.

The reactions leading to the compounds of the present invention are unique in that they appear to selectively take place at the $C_3'$ position of the macrolide in spite of the presence of other functional groups present which could potentially react under the conditions of reductive amination and hydride reduction. This lack of participation by other functional groups is unexpected.

As previously indicated, the compounds of the present invention are useful antibacterial agents. Preferred in that regard are those compounds of the formula

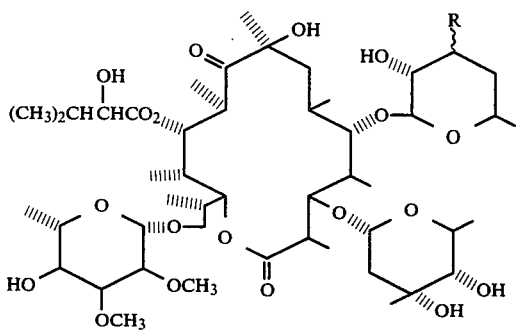

wherein R is dimethylamino. Especially preferred is the compound of the beta configuration:

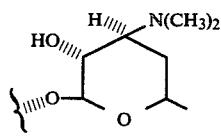

Compound 5 demonstrates enhanced activity over the parent macrolide against Hemophilus and an increase in the plasma half-life.

In the utilization of the chemotherapeutic activity of those compounds of the present invention which form salts, it is preferred, of course, to use pharmaceutically-acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically-acceptable bases by decomposition of the salt or, alternately, they can be converted to any desired pharmaceutically-acceptable acid addition salt.

Examples of acids which provide pharmaceutically-acceptable anions are hydrochloric, hydrobromic, hydroiodic, nitric, sulfuric, or sulfurous, phosphoric, acetic, lactic, citric, tartaric, succinic, maleic, gluconic and aspartic acids.

The novel derivatives described herein exhibit in vitro activity against a variety of Gram-positive microorganisms such as *Staphylococcus aureus* and *Streptococcus pyogenes* and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sickroom utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solents, such as water, alcohol, glycols or mixtures thereof or other pharmaceutically-acceptable inert media; that is, media which have no harmful effect on the active ingredient. For such purposes, it will be generally acceptable to employ concentrations of active ingredients of from about 0.01 percent to about 10 percent by weight based on total composition.

Additionally, many compounds of this invention are active versus Gram-positive and certain Gram-negative microorganism in vivo such as *Staphylococcus aureus* via the parenteral route of administration in animals, including man. Their in vivo activity is more limited as regards susceptible organisms and is determined by the usual procedure which comprises mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour postinoculation, and is repeated 4, 24 and 48 hours later. Surviving mice are held for four days after the last treatment and the number of survivors is noted.

When used in vivo, the novel compounds of the present invention wherein R is hydroxy can be administered orally or parenterally. Those novel compounds wherein R is amino, methylamino and dimethylamino are best administered parenterally, i.e., by subcutaneous or intramuscular injection. The effective oral or parenteral dose is generally from about 1 mg/kg to about 200 mg/kg of body weight per day. The favored dosage range is from about 5 mg/kg to about 100 mg/kg of body weight per day and the preferred range from about 5 mg/kg to about 50 mg/kg of body weight per day. Vehicles suitable for parenteral injection may be either aqueous such as water, isotonic saline, isotonic dextrose, Ringers' solution, or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and are not to be construed as limitations of this invention, many variations of which are possible without departing from the spirit or scope thereof.

EXAMPLE 1

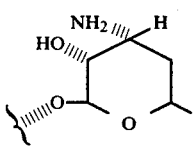

(Compound 1, R = alpha NH₂—)

A mixture of 100 mg (0.1 mmole) of CP-63,693, 53 mg (1 mmole) of ammonium chloride and 50 mg of 10% palladium-on-charcoal in 5 ml of methanol was shaken in an atmosphere of hydrogen gas at room temperature at an initial pressure of 146 kg. s. cm. After 18 hours the reaction mixture was filtered and the filtrate concentrated in vacuo to a foam. The residue was dissolved in a mixture of ethyl acetate-water and the pH adjust to 2.5 with 6N hydrochloric acid. The aqueous phase was separated and aqueous 0.1N sodium hydroxide added until the pH was 5.0. Fresh ethyl acetate was added and the mixture shaken. The aqueous layer was separated and the pH adjusted to 9.5 with 0.1N aqueous sodium hydroxide. Again, fresh ethyl acetate was added and the mixture shaken. The organic phase was separated, dried and concentrated under vacuum to give 60 mg of the desired product.

| Mass Spectrum: M/E | Cal'd for | Assignment |
| --- | --- | --- |
| 175.0963 (±0.7 ppm) | $C_8H_{15}O_4$ | mycinose sugar |
| 145.0854 (±1.1 ppm) | $C_7H_{13}O_3$ | cladinose sugar |
| 130.0867 (±0.0 ppm) | $C_6H_{12}NO_2$ | 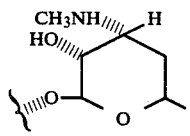 |

EXAMPLE 2

CH₃NH////H
HO////
\\\\\O—\_O (Compound 1, R = alpha CH₃NH—)

To 500 mg (0.51 mmole) of CP-63,693 and 500 mg (7.4 mmoles) of methylamine hydrochloride in 15 ml of methanol was added 100 mg of 10% palladium-on-charcoal, and the resulting mixture shaken in a hydrogen atmosphere at room temperature and an initial pressure of 146 kg. s. cm. for 18 hours. The mixture was filtered and the filtrate concentrated in vacuo to dryness. The residue was dissolved in a mixture of water-ethyl acetate and the pH adjusted to 3.0 with 6N hydrochloric acid. The aqueous phase was separated, the pH adjusted to 10 and shaken with fresh ethyl acetate. The organic phase was separated, dried and concentrated to give 460 mg of the crude product. Recrystallization from diethyl ether gave 230 mg of pure product. An additional 170 mg of product was obtained by careful concentration of the mother liquor.

| Mass Spectrum: M/e | Calc'd for | Assignment |
| --- | --- | --- |
| 144.1023 | $C_7H_{14}NO_2$ | 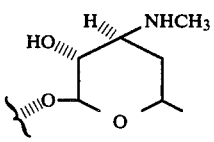 |
| NMR (CDCl₃) | δ 2.35 (s,3H) | NHCH₃ |
|  | 3.48 (s,3H) | } mycinose OCH₃ |
|  | 3.60 (s,3H) |  |

EXAMPLE 3

H////NHCH₃
HO////
\\\\\O—\_O (Compound 2, R = beta CH₃NH—)

To 500 mg (0.51 mmole) of CP-63,693 in 15 ml of methanol was added 500 mg (7.4 mmoles) of methylamine hydrochloride and the mixture allowed to stand at room temperature for 20 minutes. To the resulting solution was added 50 mg (0.79 mmole) of sodium cyanoborohydride and the reaction mixture allowed to stir for 60 minutes at room temperature. The reaction mixture was treated with water and ethyl acetate and the pH adjusted to 9.5 with 1N aqueous sodium hydroxide solution. The organic phase was separated, combined with water, and the pH adjusted to 2.5. The aqueous phase was extracted with fresh ethyl acetate at pH 5.5, 6.5, 7.0, 7.4, 7.8 and 10. The ethyl acetate from the extraction at 10 was dried and concentrated in vacuo to give 90 mg of the desired product.

| Mass Spectrum: M/e | Calc'd for | Assignment |
| --- | --- | --- |
| 144.1010 (±1.5 ppm) | $C_7H_{14}NO_2$ | 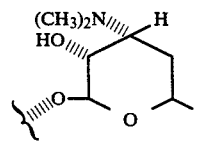 |
| NMR (CDCl₃) | δ 2.38 (s,3H) | NHCH₃ |
|  | 3.48 (s,3H) | } mycinose OCH₃ |
|  | 3.61 (s,3H) |  |

EXAMPLE 4

(CH₃)₂N////H
HO////
\\\\\O—\_O

-continued (Compound 4, R = alpha —N(CH₃)₂)

The product of Example 2 (170 mg, 0.17 mmole), 0.14 ml (1.7 mmoles) of 37% aqueous formaldehyde and 1.7 ml (0.17 mmole) of 0.1M formic acid in chloroform were added to 5 ml of chloroform and the reaction mixture allowed to stir at room temperature for 60 minutes. The reaction was diluted with water and the pH adjusted to 9.5 with 1N aqueous sodium hydroxide. The organic layer was separated, dried and concentrated under vacuum to give 170 mg (Compound 3).

The residue was dissolved in 10 ml of methanol to which was subsequently added 100 mg of 10% palladium-on-charcoal. The resulting mixture was shaken in a hydrogen atmosphere at an initial pressure of 50 p.s.i. After 18 hours the catalyst was filtered and the filtrate concentrated in vacuo to dryness. The residue was dissolved in ethyl acetate to which was added water, and the pH adjusted to 2.5 with 1N hydrochloric acid. The aqueous phase was separated and extracted with fresh ethyl acetate at pH 5.5, 6.2 and 10. The organic phase from extraction at pH 10 was dried and concentrated to give 120 mg of the desired product.

| Mass Spectrum: M/e | Calc'd for | Assignment |
|---|---|---|
| 158.1168 (±1.3 ppm) | C₈H₁₆NO₂ | 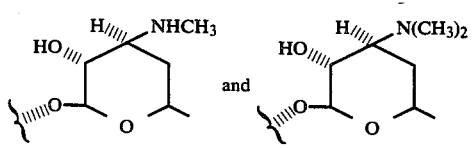 |

NMR (CDCl₃)   δ
             2.3 (s,6H) N(CH₃)₂

EXAMPLE 5

(Compound 2, R = beta —NHCH₃)   and   (Compound 5, R = beta —N(CH₃)₂)

To 15 ml of methanol was added 500 mg (0.51 mmole) of CP-63,693 and 500 mg (7.4 mmoles) of methylamine hydrochloride. After stirring at room temperature for 15 minutes 50 mg (0.79 mmole) of sodium borohydride was added and the resulting reaction mixture allowed to stir at ambient temperature for 2 hours. The reaction mixture was treated with water and ethyl acetate and the pH adjusted to 10 with 1N aqueous sodium hydroxide. The organic layer was separated, dried and concentrated to dryness. The residue was dissolved in fresh ethyl acetate, water added and the pH adjusted to 2.5. The aqueous phase was separated, combined with fresh ethyl acetate and the pH adjusted to 10. The organic phase was separated, dried and concentrated to give 380 mg of product which, by thin layer chromatography, contains the two C₃' diastereomers 1 and 2 (R¹=CH₃).

To the residue was added 5 ml of chloroform and 0.3 ml of 37% formaldehyde solution and the solution allowed to stir for 60 minutes at room temperature. Water was added and the pH adjusted to 2.5. The aqueous phase was separated, treated with ethyl acetate and the pH raised to 10.0 with 1N aqueous sodium hydroxide. The organic phase was separated, dried and concentrated in vacuo to give 130 mg of product (compound 2, R=beta —NHCH₃).

The residue was combined with 2.6 ml (0.26 mmole) of 0.1M formic acid in chloroform and 5 drops of 37% formaldehyde and the reaction mixture heated to reflux for 2 hours. The reaction was treated with water, the pH adjusted to 3.0 and ethyl acetate added. The pH was adjusted to 10 and the organic layer separated, dried and concentrated in vacuo to give 60 mg of the final product (compound 5, R=beta —N(CH₃)₂).

| Mass Spectrum (cpd 5) M/e | Calc'd for | Assignment |
|---|---|---|
| 158.1181 | C₈H₁₆O₂N | 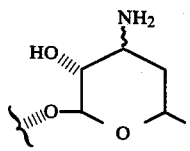 |

NMR (CDCl₃)   δ
             2.28 (s,6H)  } N(CH₃)₂
             3.48 (s,3H)  } mycinose OCH₃
             3.62 (s,3H)  }

EXAMPLE 6

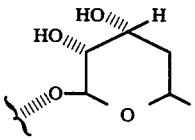

Diastereomers 1 and 2, R = NH₂

The procedure of Example 3 is repeated starting with 500 mg (0.51 mmole) of CP-63,693, 39.8 mg (0.75 mmole) of ammonium chloride, 50 mg of sodium cyanoborohydride and 15 ml of methanol. On completion of the reaction water and ethyl acetate are added to the reaction and the pH adjusted to 9.5. The ethyl acetate layer is separated, dried and concentrated under vacuum to give a mixture of the alpha and beta diastereomers, 1 and 2, R=NH₂.

EXAMPLE 7

(Compound 7, R = alpha —OH)

A mixture of 100 mg (0.1 mmole) of CP-63,693 and 52 mg (0.2 mmole) of lithium tri-t-butoxyaluminumhydride in 10 ml of tetrahydrofuran was allowed to stir at room temperature for 1 hour. The reaction mixture was treated with water and ethyl acetate and the pH adjusted to 10. The ethyl acetate was separated and the aqueous layer extracted (3x) with fresh ethyl acetate. The organic extracts were combined, dried over sodium sulfate and concentrated to give 90 mg of product.

| Mass Spectrum: M/e | Calc'd for | Assignment |
|---|---|---|
| 131.0704 (±0.4 ppm) | $C_6H_{11}O_3$ | 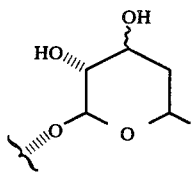 |

| NMR: | δ | |
|---|---|---|
| | 3.52 (s,3H) | mycinose OCH$_3$ |
| | 3.65 (s,3H) | |

EXAMPLE 8

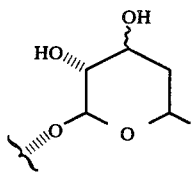

Diastereomers 6 and 7, R = OH

To a solution of 100 mg (0.1 mmole) of CP-63,693 in 5 ml of tetrahydrofuran was added 3.8 mg (0.025 mmole) of sodium borohydride and the resulting reaction mixture allowed to stir at room temperature for 1 hour. The solvent was evaporated and the residue dissolved in 50 ml of ethyl acetate-water (1:1, v:v). The organic phase was separated, dried and concentrated to give 89 mg of an amorphous solid which, by thin layer chromatography (chloroform-methanol-ammonium hydroxide; 5:1:1) indicated a 50—50 mixture of the desired two diastereomers.

| Mass Spectrum: M/e | Calc'd for | Assignment |
|---|---|---|
| 131.0704 (±0.4 ppm) | $C_6H_{11}O_3$ | |

I claim:
1. A compound of the formula

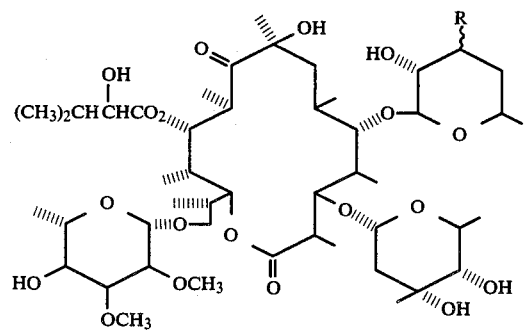

wherein R is selected from the group consisting of hydroxy, amino, methylamino and dimethylamino, and the pharmaceutically-acceptable acid addition salts of those wherein R is amino, methylamino or dimethylamino.

2. A compound of claim 1, wherein R is dimethylamino.

3. The compound of claim 2, wherein R is beta dimethylamino.

4. A method for treating a bacterial infection in a mammalian subject, which comprises administering to said subject an antibacterially effective amount of a compound according to claim 1.

* * * * *